United States Patent [19]

Takahashi et al.

[11] Patent Number: 5,191,136
[45] Date of Patent: * Mar. 2, 1993

[54] PROCESS FOR PRODUCTION OF SEC-BUTYLBENZENE

[75] Inventors: Kazuteru Takahashi, Chiba; Yasuhiko Higashio, Osaka, both of Japan

[73] Assignee: Sumitomo Chemical Co., Ltd., Osaka, Japan

[ * ] Notice: The portion of the term of this patent subsequent to Oct. 22, 2008 has been disclaimed.

[21] Appl. No.: 756,692

[22] Filed: Sep. 9, 1991

[30] Foreign Application Priority Data

Sep. 10, 1990 [JP] Japan .................................. 2-240670
Jun. 3, 1991 [JP] Japan .................................. 3-131092

[51] Int. Cl.$^5$ ................................................ C07C 2/70
[52] U.S. Cl. ................................ 585/461; 585/459; 585/462
[58] Field of Search ........................ 585/459, 461, 462

[56] References Cited

U.S. PATENT DOCUMENTS

| | | | |
|---|---|---|---|
| 3,303,230 | 2/1967 | McMinn, Jr. | 585/461 |
| 3,819,735 | 6/1974 | Argento et al. | 585/461 |
| 4,287,074 | 9/1981 | Earhart et al. | 585/461 |

FOREIGN PATENT DOCUMENTS

| | | |
|---|---|---|
| 0395360 | 10/1990 | European Pat. Off. |
| 945326 | 7/1956 | Fed. Rep. of Germany . |
| 2421168 | 5/1978 | Fed. Rep. of Germany . |
| 50-137933 | 11/1975 | Japan . |
| 3-47139 | 2/1991 | Japan . |
| 1109578 | 4/1968 | United Kingdom . |

*Primary Examiner*—Patrick P. Garvin
*Assistant Examiner*—E. D. Irzinski
*Attorney, Agent, or Firm*—Sughrue, Mion, Zinn, Macpeak & Seas

[57] ABSTRACT

A process for production of sec-butylbenzene is disclosed, comprising reacting benzene and n-butene in the presence of a liquid aluminum chloride complex catalyst is disclosed, wherein the reaction is carried out under conditions satisfying formulae (1) to (4):

$$40 > C \times T \times 2^{(K-20)/10} > \quad (1)$$

$$C \leq 0.9 \quad (2)$$

$$T \leq 0.7 \quad (3)$$

$$K \geq 80 \quad (4)$$

wherein C is a concentration (% by weight) of a complex catalyst in the reaction mixture; T is a reaction time (hr); and K is a reaction temperature (°C). sec-Butylbenzene is produced in high yield while suppressing the amount of isobutylbenzene formed as a by-product.

6 Claims, No Drawings

PROCESS FOR PRODUCTION OF SEC-BUTYLBENZENE

FIELD OF THE INVENTION

The present invention relates to a process for production of sec-butylbenzene from benzene and n-butene. sec-Butylbenzene produced by the present invention is particularly useful for use as a starting material for production of phenol and methyl ethyl ketone through the respective steps of air oxidation and decomposition.

Phenol can be used as a starting material for production of synthetic resins and antioxidants, and methyl ethyl ketone can be used as a solvent or for dewaxing of lubricating oils.

BACKGROUND OF THE INVENTION

Use of a liquid aluminum chloride complex catalyst in production of sec-butylbenzene from benzene and n-butene has heretofore been known. For example, JP-A-50-137933 (the term "JP-A" as used herein means an "unexamined published Japanese patent application") discloses a method in which a liquid aluminum chloride complex catalyst is used in such an amount that the amount of aluminum chloride is from 0.05 to 0.25% by weight of the reaction mixture.

In production of sec-butylbenzene from benzene and n-butene by an alkylation method, the product is a mixture mainly containing sec-butylbenzene (SBB), isobutylbenzene (IBB), disec-butylbenzene (DSBB), and tri-sec-butylbenzene (TSBB).

Of these compounds, di-sec-butylbenzene and tri-sec-butylbenzene are each separated from the reaction mixture and then transalkylated into sec-butylbenzene. This reaction can be illustrated as follows:

$$C_6H_4(C_4H_9)_2 + C_6H_6 \longrightarrow 2.\text{sec-}C_6H_5C_4H_9$$
$$\text{DSBB} \quad\quad \text{benzene} \quad\quad\quad \text{SBB}$$

$$C_6H_3(C_4H_9)_3 + 2C_6H_6 \longrightarrow 3.\text{sec-}C_6H_5C_4H_9$$
$$\text{TSBB} \quad\quad \text{benzene} \quad\quad\quad \text{SBB}$$

Boiling points of isobutylbenzene and sec-butylbenzene are 172.8° C. and 173.5° C., respectively, and are close to each other. Thus it is difficult to separate these two compounds from each other by distillation. Isobutylbenzene formed as a by-product in the reaction is sent as such to an air oxidation step along with sec-butylbenzene. It is known, however, that if sec-butylbenzene contains isobutylbenzene, the rate of reaction in the air oxidation step is markedly decreased (see JP-A-48-80524). For example, the rate of air oxidation of sec-butylbenzene, when the sec-butylbenzene contains 1% by weight of isobutylbenzene, decreases to about 91% of that when the sec-butylbenzene does not contain isobutylbenzene at all. Similarly, when the isobutylbenzene content is 1.65% by weight, the rate of air oxidation decreases to about 86%; when the isobutylbenzene content is 2% by weight, the rate of air oxidation decreases to about 84%; and when the isobutylbenzene content is 3.5% by weight, the rate of air oxidation decreases to as much as about 82%. Therefore, in order to efficiently undergo the air oxidation step, it is necessary to use secbutylbenzene having a decreased isobutylbenzene content as much as possible. For this reason, the amount of isobutylbenzene formed as a by-product at the step of production of secbutylbenzene from benzene and n-butene is needed to minimize.

However, when conventional alkylation methods are followed, maintenance of a satisfactory level of the yield of the desired sec-butylbenzene is attended by an increased proportion of isobutylbenzene formed as a by-product, reaching 1 to 4% by weight based on the desired sec-butylbenzene, and such a large amount of isobutylbenzene formed as a by-product has been subjected to air oxidation without being removed.

SUMMARY OF THE INVENTION

An object of the present invention is to provide a process for production of sec-butylbenzene in good yield while suppressing the amount of isobutylbenzene formed as a byproduct.

In the light of the above object, the inventors have conducted extensive investigations and, as a result, found that the object can be accomplished by optimum selection of a catalyst amount, a reaction temperature, and a reaction time and thus completed the present invention.

The present invention relates to a process for production of sec-butylbenzene comprising reacting benzene and n-butene in the presence of a liquid aluminum chloride complex catalyst, wherein the reaction is carried out under conditions satisfying formulae (1) to (4):

$$40 > C \times T \times 2^{(K-20)/10} > 20 \tag{1}$$

$$C \leq 0.9 \tag{2}$$

$$T \leq 0.7 \tag{3}$$

$$K \geq 80 \tag{4}$$

wherein C is a concentration (% by weight) of a complex catalyst in the reaction mixture; T is a reaction time (hr); and K is a reaction temperature (°C.).

DETAILED DESCRIPTION OF THE INVENTION

The liquid aluminum chloride complex catalyst (hereinafter simply referred to as a complex catalyst) which can be used in the present invention is a uniform solution type complex catalyst composed of aluminum chloride, hydrogen chloride, and an aromatic hydrocarbon. Aromatic hydrocarbons usable here include sec-butylbenzene, ethylbenzene, di-secbutylbenzene, and tri-sec-butylbenzene, and mixtures of two or more thereof, with sec-butylbenzene being the most suitable.

Hydrogen chloride and the aromatic hydrocarbon are used in an amount of about 1 mole and from 2 to 10 mole, respectively, per mole of aluminum chloride.

The complex catalyst is prepared simply by mixing these components with stirring to prepare a uniform solution. Such can be done by stirring at room temperature for about 20 minutes to 3 hours. In some cases, the complex catalyst may be prepared by reacting metallic aluminum and hydrogen chloride in an aromatic hydrocarbon. The thus obtained complex catalyst can be used as such in the reaction of benzene and n-butene.

The catalyst once used in the reaction may be separated from the reaction mixture and then reused.

The complex catalyst is a complex comprising 0.5 mole of hydrogen chloride and 2 mole of an aromatic hydrocarbon having one mole of aluminum chloride bonded thereto. The terminology "concentration of a complex catalyst (C% by weight) in the reaction mixture" is expressed in terms of concentration of such a complex catalyst in the reaction mixture.

n-Butene which can be used in the present invention includes 1-butene, cis-2-butene, trans-2-butene, and a mixture thereof. Further, a mixture of n-butene and a compound inert to the reaction, e.g., butane, may also be used.

The process of the present invention can be carried out by mixing benzene, n-butene, and the above-described complex catalyst by stirring. n-Butene is preferably used in an amount of from 0.2 to 1.2 mole, and more preferably from 0.4 to 1.1 mole, per mole of benzene. If the amount of n-benzene is too small, the volumetric efficiency of the reaction decreases, and the cost for separating sec-butylbenzene from the reaction mixture increases. On the other hand, it the amount is too large, the amount of benzene species having two or more butyl groups formed as by-products would be increased.

In the present invention, in order to prepare secbutylbenzene while suppressing the amount of isobutylbenzene formed as a by-product, the reaction must be conducted under such conditions that the complex catalyst concentration in the reaction mixture (C% by weight), reaction time (T hr), and reaction temperature (K°C.) satisfy the above-described formulae (1) to (4).

That is, upper limits of $C \times T \times 2^{(K-20)/10}$, C, and T are specified for suppressing the amount of isobutylbenzene formed as a by-product, while lower limits of $C \times T \times 2^{(K-20)/10}$, C, and T are specified for attaining satisfactory yield of sec-butylbenzene.

While the complex catalyst concentration, reaction time, and reaction temperature can be arbitrarily selected from the respective ranges as above specified, the complex catalyst concentration in the reaction mixture usually ranges from 0.01 to 0.9% by weight; the reaction time usually ranges from 0.01 to 0.7 hour; and the reaction temperature usually ranges from 80° to 150° C., and preferably from 90° to 120° C.

The term "reaction time" as used herein means the time during which the complex catalyst, benzene, and n-butene are in contact with each other under the reaction conditions employed. In case where the reaction is performed in a continuous system, the reaction time means a so-called average retention time. The reaction pressure is not particularly limited.

The reaction may be effected either batchwise or continuously. In the latter case, a continuous stirring multireactor system is preferably employed.

According to the process of the present invention, the amount of isobutylbenzene formed as a by-product can be controlled to 1% by weight or less based on the produced secbutylbenzene. The importance of reduction of the isobutylbenzene/sec-butylbenzene production ratio is as previously discussed.

Separation and recovery of sec-butylbenzene from the reaction mixture are achieved in a usual manner. For example, the complex catalyst is removed from the reaction mixture by liquid separation, or the complex catalyst while being present in the reaction mixture is inactivated by washing the reaction mixture with water and then removed therefrom. The mother liquor is further washed with a sodium hydroxide aqueous solution to completely remove any remaining complex catalyst, followed by separation into an oily phase and an aqueous phase. The oily phase separated is distilled to separate into a fraction mainly comprising sec-butylbenzene, a fraction mainly comprising di-sec-butylbenzene and tri-sec-butylbenzene, a fraction mainly comprising unreacted benzene, and a fraction mainly comprising heavy materials. If desired, the fraction mainly comprising di-sec-butylbenzene and tri-sec-butylbenzene may be subjected to the above-described trans-alkylation to obtain sec-butylbenzene. The unreacted benzene may be reused by recycling to the reaction zone for preparing sec-butylbenzene from benzene and n-butene.

It is recommended to recycle the fraction mainly comprising di-sec-butylbenzene and tri-sec-butylbenzene to the reaction zone of benzene and n-butene together with the separated benzene.

It is also recommended that the spent complex catalyst be recovered from the reaction mixture by liquid separation and recycled to the reaction zone of benzene and n-butene.

sec-Butylbenzene obtained in the process of the present invention is suitably used as a starting material for production of phenol. Processes for producing phenol from sec-butylbenzene include the process disclosed in JP-A-48-80524 in which sec-butylbenzene is oxidized at about 75° to 140° C., and the resulting sec-butylbenzene hydroperoxide is concentrated and then subjected to decomposition in the presence of an acid catalyst to obtain phenol and methyl ethyl ketone.

The present invention is now illustrated in greater detail with reference to the following examples, but it should be understood that the present invention is not deemed to be limited thereto. All the percents, parts, and ratios are by weight unless otherwise indicated.

EXAMPLE 1

In a 200 ml three-necked flask equipped with a stirrer and an inlet pipe for gas blowing were charged 61.64 g of secbutylbenzene and 26.79 g of aluminum chloride. Hydrogen chloride gas was then blown thereinto from the inlet pipe with stirring over 2 hours. The aluminum chloride was dissolved in sec-butylbenzene with time, finally giving 95 g of a liquid aluminum chloride complex catalyst as a uniform solution (aluminum chloride concentration: 28%).

In a separate 200 ml three-necked flask equipped with a stirrer and an inlet pipe for gas blowing were continuously fed 161 g/hr of benzene, 58 g/hr of 1-butene, and 1.84 g/hr of the above-prepared complex catalyst (the complex catalyst concentration in the reaction mixture was 0.84%) while maintaining the inner temperature at 80° C. by heating the flask on a warm water bath. The flask used had an overflow pipe at the level of 170 ml, through which the reaction mixture was continuously withdrawn. The average retention time of the mixture was 0.67 hour, and the value $C \times T \times 2^{(k-20)/10}$ was 36.0. The thus withdrawn reaction mixture was analyzed by gas chromatography using a DB-1 capillary column (60 m in length) at a temperature increasing from 100° C. (at which the reaction mixture was kept for 10 minutes) to 200° C. at a rate of 10° C./min. The results of analysis on the reaction mixture obtained after 8 hours from the start of the reaction are shown in Table 1.

EXAMPLES 2 TO 3 AND COMPARATIVE EXAMPLES 1 TO 2

The same procedures of Example 1 were repeated, except for changing the feed rate of the complex catalyst and the reaction temperature as shown in Table 1 below. The results obtained are shown in Table 1.

EXAMPLE 4

A liquid aluminum chloride complex catalyst was prepared in the same manner as in Example 1. To a 200 ml glass-made autoclave equipped with a stirrer were continuously fed 644 g/hr of benzene, 232 g/hr of 1-butene, and 1.84 g/hr of the complex catalyst (the complex catalyst concentration in the reaction mixture was 0.21%) while maintaining the inner temperature and pressure at 120° C. and 3 kg/cm$^2$ by heating the autoclave by means of a heater. The autoclave used had an overflow pipe at the level of 170 ml, through which the reaction mixture was continuously withdrawn. The thus withdrawn reaction mixture was analyzed by gas chromatography in the same manner as in Example 1. The results obtained are shown in Table 1.

COMPARATIVE EXAMPLE 3

The same procedures of Example 4 were repeated, except for changing the feed rate of the complex catalyst and the reaction temperature as shown in Table 1. The results obtained are shown in Table 1.

EXAMPLE 5

The same procedures of Example 1 were repeated, except for changing the feed rate of the complex catalyst and the reaction temperature as shown in Table 1 and replacing the 1-butene with mixed butene comprising 38% of 1-butene, 8% of cis-2-butene, 16% of trans-2-butene, 12% of isobutane, and 26% of n-butane. The results obtained are shown in Table 1.

EXAMPLE 6

A 200 ml three-necked flask (flask 1) equipped with a stirrer and an inlet pipe for gas blowing and a 200 ml three-necked flask (flask 2) equipped with a stirrer were connected in series via an overflow pipe provided at the level of 170 ml of flask 1. To flask 1 were continuously fed 322 g/hr of benzene, 116 g/hr of 1-butene, and 1.84 g/hr of a complex catalyst prepared in the same manner as in Example 1 (the complex catalyst concentration in the reaction mixture was 0.42%). The reaction mixture in flask 1 was continuously transferred to flask 2 through the overflow pipe. Flask 2 also had an overflow pipe at the level of 170 ml, and the reaction mixture in flask 2 was also continuously withdrawn therethrough. The average total retention time of the reaction mixture in the two flasks was 0.67 hour, and the value $C \times T > 2^{(K-20)/1}$ was 36.0.

The reaction temperature in both flask 1 and flask 2 was maintained at 90° C. by means of a warm water bath.

The thus withdrawn reaction mixture from flask 2 was analyzed by gas chromatography under the same conditions as in Example 1. The results of analysis on the reaction mixture obtained after 15 hours from the start of the reaction are shown in Table 1.

TABLE 1

| | Example 1 | Example 2 | Example 3 | Example 4 | Compar. Example 1 | Compar. Example 2 | Compar. Example 3 | Example 5 | Example 6*[6] |
|---|---|---|---|---|---|---|---|---|---|
| Reaction Conditions: | | | | | | | | | |
| Feed rate (g/hr): | | | | | | | | | |
| Benzene | 161 | 161 | 161 | 644 | 161 | 161 | 74 | 161 | 322 |
| 1-Butene | 58 | 58 | 87 | 232 | 58 | 58 | 11 | 94*[5] | 116 |
| C (%) | 0.84 | 0.42 | 0.37 | 0.21 | 1.26 | 0.84 | 0.11 | 0.37 | 0.42 |
| T (hr) | 0.67 | 0.67 | 0.67 | 0.17 | 0.67 | 0.67 | 2.00 | 0.67 | 0.67 |
| K (°C.) | 80 | 90 | 90 | 120 | 90 | 50 | 120 | 90 | 90 |
| $C \times T \times 2^{(K-20)/10}$ | 36.0 | 36.0 | 31.7 | 36.6 | 108.1 | 4.5 | 225.3 | 31.7 | 36.0 |
| Reaction Mixture Composition (%): | | | | | | | | | |
| Benzene | 39.3 | 40.8 | 24.7 | 39.7 | 38.1 | 70.2 | 70.0 | 38.6 | 38.9 |
| SBB*[1] | 46.9 | 47.0 | 53.1 | 48.0 | 46.5 | 26.2 | 26.7 | 47.8 | 47.8 |
| IBB*[2] | 0.45 | 0.41 | 0.51 | 0.44 | 1.22 | 0.24 | 1.10 | 0.40 | 0.46 |
| DSBB*[3] | 10.5 | 11.2 | 21.8 | 9.9 | 10.6 | 3.0 | 2.0 | 9.2 | 11.7 |
| IBB/SBB (%) | 0.96 | 0.87 | 0.96 | 0.92 | 2.62 | 0.91 | 4.12 | 0.84 | 0.96 |
| SBB Concentration at Equilibrium (%)*[4] | 48.0 | 48.0 | 54.0 | 48.0 | 48.0 | 48.0 | 27.0 | 48.0 | 48.0 |

Note:
*[1] sec-Butylbenzene
*[2] Isobutylbenzene
*[3] Di-sec-butylbenzene
*[4] Maximum concentration at equilibrium (theoretical value)
*[5] Mixed butene was used in place of the 1-butene.
*[6] Two reactors connected in series were used.

As can be seen from the results in Table 1, in all the examples in which the reaction was carried out under specific conditions according to the present invention, the reaction showed sufficient progress (high benzene conversion) with a reduced amount of undesired isobutylbenzene formed as a byproduct, and the object of the present invention was sufficiently achieved.

To the contrary, in Comparative Example 3 where $C \times T \times 2^{(K-20)/10}$ and T (reaction time) exceeded the respective upper limits of the ranges specified in the present invention and in Comparative Example 1 wherein $C \times T \times 2^{(K-20)/10}$ and C (catalyst concentration) exceeded the respective upper limits of the ranges specified in the present invention, formation of undesired isobutylbenzene as a by-product was remarkably observed. Further, in Comparative Example 2 wherein $C \times T \times 2^{(K-20)/10}$ and T (reaction time) were less than the respective lower limits of the ranges specified in the present invention, there was observed a large difference between the sec-butylbenzene concentration in the reaction mixture and that at equilibrium, revealing insufficient reaction progress (insufficient benzene conversion).

As stated above, the present invention provides a process for production of sec-butylbenzene from benzene and n-butene in which sufficient reaction progress can be assured while suppressing a production ratio of undesired isobutylbenzene as a by-product to sec-butylbenzene.

While the invention has been described in detail and with reference to specific examples thereof, it will be apparent to one skilled in the art that various changes and modifications can be made therein without departing from the spirit and scope thereof.

What is claimed is:

1. A process for production of sec-butylbenzene comprising reacting benzene and n-butene in the presence of a liquid aluminum chloride complex catalyst, wherein the reaction is carried out under conditions satisfying formulae (1) to (4):

$$40 > C \times T \times 2^{(K-20)/10} > 20 \quad (1)$$

$$C \leq 0.9 \quad (2)$$

$$T \leq 0.7 \quad (3)$$

$$K \geq 80 \quad (4)$$

wherein C is a concentration (% by weight) of a complex catalyst in the reaction mixture; T is a reaction time (hr); and K is a reaction temperature (°C.).

2. A process as claimed in claim 1, wherein a molar ratio of benzene and n-butene charged is from 1:0.2 to 1:1.2.

3. A process as claimed in claim 2, wherein a molar ratio of benzene and n-butene charged is from 1:0.4 to 1:1.1.

4. A process as claimed in claim 1, wherein a reaction mixture obtained is separated into a fraction mainly comprising unreacted benzene, a fraction mainly comprising sec-butylbenzene, a fraction mainly comprising di-sec-butylbenzene and tri-sec-butylbenzene, and a fraction mainly comprising heavy materials.

5. A process as claimed in claim 4, wherein said fraction mainly comprising unreacted benzene and fraction mainly comprising di-sec-butylbenzene and tri-sec-butylbenzene are recycled to the reaction zone.

6. A process as claimed in claim 1, wherein sec-butylbenzene obtained is sec-butylbenzene to be used as a starting material for production of phenol.

* * * * *